United States Patent [19]
Becker

[11] 4,274,850
[45] Jun. 23, 1981

[54] RECTIFICATION OF NATURAL GAS

[75] Inventor: Hans Becker, Munich, Fed. Rep. of Germany

[73] Assignee: Linde Aktiengesellschaft, Wiesbaden, Fed. Rep. of Germany

[21] Appl. No.: 94,262

[22] Filed: Nov. 14, 1979

[30] Foreign Application Priority Data

Nov. 14, 1978 [DE] Fed. Rep. of Germany ....... 2849344

[51] Int. Cl.³ ............................................. F25J 3/02
[52] U.S. Cl. ............................................. 62/24; 62/38; 62/28
[58] Field of Search .................... 62/24, 28, 38, 39, 31

[56] References Cited

U.S. PATENT DOCUMENTS

| | | | |
|---|---|---|---|
| 2,557,171 | 6/1951 | Bodle et al. | 62/39 |
| 2,823,523 | 2/1958 | Eakin et al. | 62/39 |
| 3,397,138 | 8/1968 | Bacon | 62/38 |
| 3,559,418 | 2/1971 | Hoffman | 62/24 |
| 4,061,481 | 12/1977 | Campbell et al. | 62/38 |

*Primary Examiner*—Norman Yudkoff
*Attorney, Agent, or Firm*—Millen & White

[57] ABSTRACT

For separating a $C_{2+}$-hydrocarbon fraction from compressed $CO_2$-containing natural gas by rectification, wherein the compressed natural gas is, prior to rectification, subjected to partial condensation and engine-expansion steps to achieve the desired pressure and temperature conditions in the rectification column and wherein said column is fed by resultant condensate of natural gas, the improvement comprising:

conducting the engine expansion of the natural gas to a point well above the temperature at which the $CO_2$ would otherwise precipitate out, and recovering from the engine expansion step an unliquefied gaseous fraction, and passing said fraction in indirect heat exchange relationship with engine-expanded overhead product from said column, whereby peak cooling and partial condensation of said fraction is achieved, and feeding resultant partially condensed fraction to the top of said column.

7 Claims, 1 Drawing Figure

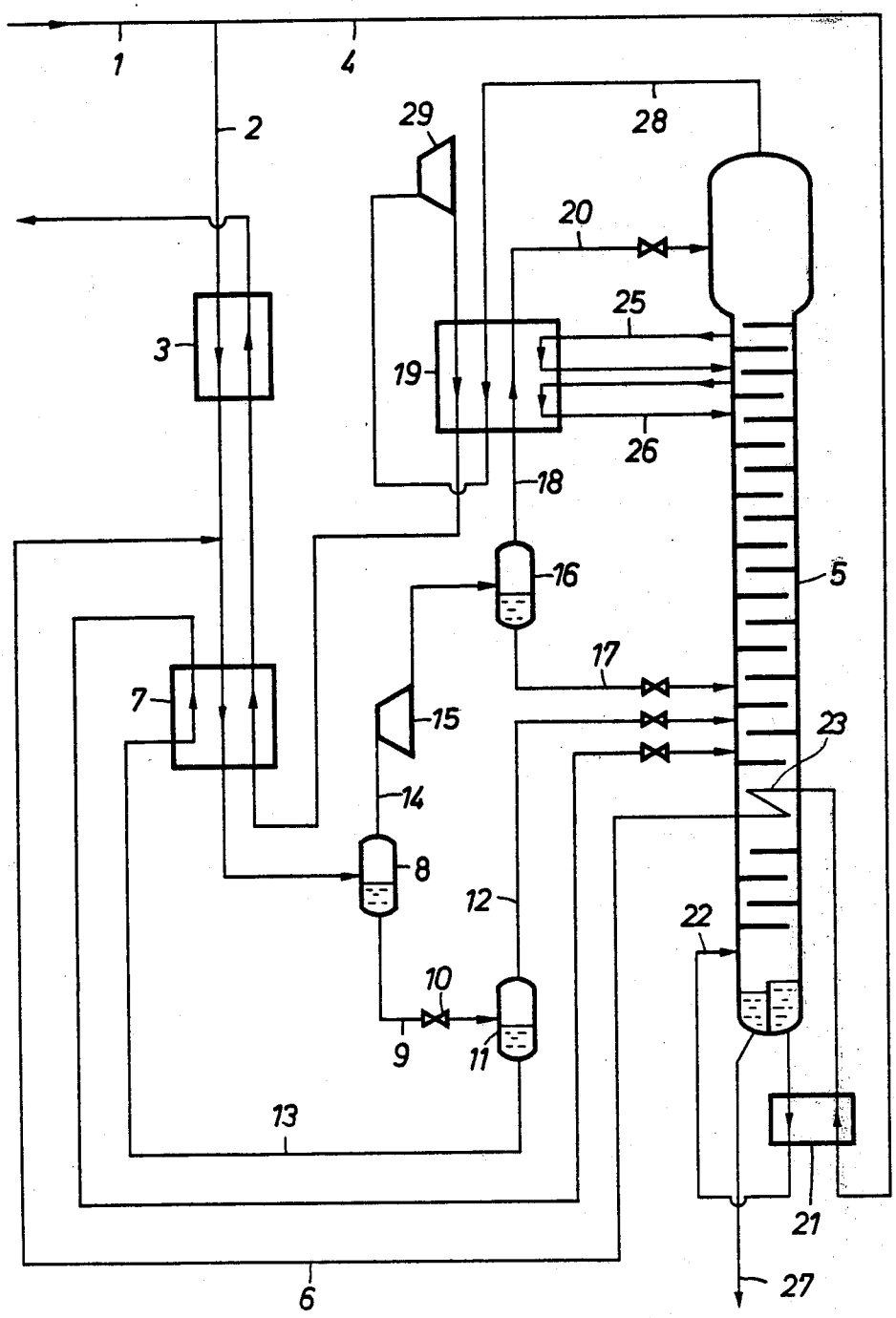

RECTIFICATION OF NATURAL GAS

BACKGROUND OF THE INVENTION

This invention relates to a process for separating a $C_{2+}$ hydrocarbon fraction from compressed natural gas by rectification, the required temperature and pressure conditions thereof being obtained by heat exchange and engine expansion and where the rectification column is fed by condensate fractions of the natural gas.

A process of this type is described in U.S. Pat. No. 3,292,380, wherein the natural gas first is cooled by heat exchange, resulting in partial condensation. The resultant liquid phase is, after pressure reduction, in part fed to the rectifying column, and the resultant gas phase is engine expanded to the pressure of the rectification column. This process, however, is disadvantageous insofar as natural gas containing carbon dioxide requires a special preliminary process step for the removal of $CO_2$. Otherwise, there would be the danger of solids precipitation and even clogging of the facility if operated at low temperatures. As regards the precipitation of solids, those parts of the facility especially jeopardized are those encountering the lowest temperatures or where the carbon dioxide is concentrated. In this known process, a particularly hazardous location is at the head of the rectification column, because the carbon dioxide concentration in the reflux liquid to the column as a rule will be higher than in the liquid at the turbine discharge.

SUMMARY OF THE INVENTION

An object of this invention is to provide an improved process of the above cited type which permits the elimination of a preliminary carbon dioxide separation step, especially with respect to the natural gas having a somewhat higher concentration in carbon dioxide.

Another object is to provide an improved process with respect to capital and energy costs.

Upon further study of the specification and appended claims, further objects and advantages of this invention will become apparent to those skilled in the art.

To attain these objects, in one aspect of this invention, after the engine-expansion step, the non-liquefied fraction natural gas is partially liquefied by heat exchange with the engine-expanded top product from the rectification column, and is then fed into the rectification column. Whereas in the known process, the lowest pressure is achieved by the turbine expansion step which also simultaneously achieves peak cooling for the rectification, the present invention separates, on the one hand, the generation of the peak cooling (to obtain the lowest temperature level required for the column), and on the other hand, the setting of the column pressure. The first turbine expansion in the present invention is conducted so that the risk of solids precipitation in the rectifier column is avoided and without reaching the low temperature required for the column-head. This peak cooling rather is achieved later by engine expansion of the residual gas drawn off the head of the rectification column.

In another advantageous aspect of this invention, the residual gas (the product leaving the top of the column comprising mostly methane) is heated prior to engine expansion to the extent that no condensate is formed during said expansion. Thus, there is ensured that in the process of this invention, a precipitate of solid carbon dioxide is avoided at the discharge end of the second turbine. The particular conditions of rectification and the composition of the natural gas determine whether this heating of the residual gas is required in order to avoid solids precipitation in each individual case. (Said conditions and composition determine, in essence, the amounts of the carbon dioxide contained in the original natural gas which are passed into the residual gas on the one hand, and into the sump product of the rectification on the other hand.) However, this heating step is also advantageous even when there is no danger of forming condensates because the energy losses in the heat exchange against the natural gas to be introduced into the rectification column can be reduced by said heating of the residual gas prior to the second turbine.

A further advantageous aspect of this invention comprises heating the residual gas by heat exchange with a gaseous fraction of that natural gas remaining after the first engine expansion step and prior to rectification of same. In this manner, the refrigerant value of the unexpanded residual gas is also utilized.

In a further aspect of the process of this invention, the exchange losses can be further reduced if part of the heat content of the gaseous flow obtained after the first engine expansion is applied to intermediate heat transfer streams derived from the rectification column. In this manner, there is achieved thermodynamically efficient matching of the Q and T functions between the gas flow to be cooled and that to be heated.

BRIEF DESCRIPTION OF THE DRAWING

The drawing is a schematic illustration of a preferred embodiment of the invention.

DETAILED DESCRIPTION OF THE DRAWING

The crude gas is introduced through conduit 1 at a pressure of 40 bars and a temperature of 292° K. This is a natural gas consisting of 1.01 mole-% of nitrogen, 81.74 mole-% of methane, 6.70 mole-% of ethane, 6.88 mole-% of propane, 2.41 mole-% of butane, 0.76 mole-% of pentane, 0.25 mole-% of hexane, 0.07 mole-% of $C_{7+}$-hydrocarbons and 0.18 mole-% of carbon dioxide. One part, e.g. 30 to 70%, of this crude gas passes through conduit 2 into a first heat exchanger 3 where it is cooled against residual gas being heated. The other portion of the crude gas is branched off through conduit 4 and used for heating the sump of the rectification column 5; the resultant cooled minor portion is then passed through conduit 6 and is remixed with the major part of the natural gas in conduit 2, whereafter the entire flow of crude gas is cooled to 242° K. in heat exchanger 7, wherein partial condensation is effected. The resultant condensate is removed in phase separator 8, drawn off through conduit 9, pressure reduced in throttle valve 10 to the pressure of the rectification column 5 and fed to another phase separator 11. The gas phase formed during pressure reduction is fed through conduit 12 directly to the rectification column 5. This fraction, as well as others not yet discussed, are introduced at locations in the column 5 adapted to equilibrium conditions therein as well as to the particular compositions of the fractions to be introduced.

The fraction remaining in the liquid phase after passing through throttle 10 is removed through conduit 13 from the phase separator 11 and is evaporated in part against crude gas in the heat exchanger 7 for the purpose of improving rectification before entering column 5.

The gaseous fraction from phase separator 8 is passed through conduit 14 to an expansion turbine 15 where it is expanded to a pressure of 16.3 bars. The gas is thereby cooled to 208° K. and forms a condensate which is removed in phase separator 16 and introduced through conduit 17 to the rectification column 5 as reflux liquid. The remaining expanded gas in phase separator 16 is passed through conduit 18 to another heat exchanger 19 where it is further cooled, a further condensate being formed in the heat exchanger. Care must be exerted that cooling is always carried so far that the desired yield in $C_{2+}$ hydrocarbons be contained in the combined condensates of separators 8 and 16 in conjunction with the part of the gas which is condensed in heat exchanger 19. This, in turn, determines the temperature which, depending on the pressure reached in the expansion 15, the gas must assume at the exit of the heat exchanger 19. In the above example, a 90% separation is desired for the ethane. This requires cooling the gas in heat exchanger 19 to 166° K. The two-phase mixture formed thereby is fed through valved conduit 20 into the top region of the column 5.

The rectification column 5 is operated at a pressure of 16 bars and in a temperature range from 166° K. at its top to 285° K. in its sump. The sump temperature is set by heating part of the sump liquid in a heat exchanger 21 against the minor part of the crude gas which was branched off through conduit 4. The heated sump product is fed back through conduit 22 into the bottom region of the rectification column 5. A further heating means 23 is provided in the lower range of column 5 where the minor fraction of crude gas carried in the conduit 4 is cooled even further. Intermediate heat transfer streams 25 and 26 are provided in the upper region of the column 5. Liquid is drawn off one column plate and heated in heat exchanger 19 against the gas to be cooled in conduit 18 before being recycled to the column 5. The $C_{2+}$-fraction, practically free of methane, collects in the sump and is drawn off through conduit 27 in an amount of 167 moles per 1,000 moles of crude gas, while at the top there is obtained through conduit 28 833 moles of residual gases containing only slight amounts of hydrocarbons with 2 or more carbon atoms.

The residual gas is first heated countercurrently to the crude gas of conduit 18 in the heat exchanger 19 to 189° K. and then expanded in an expansion turbine 29 to 5.5 bars. On the basis of the latter heating step, no condensation of $CO_2$ takes place during this engine expansion, and the gas is cooled to 151° K. Accordingly, this 151° K. gas provides the peak cooling required for rectification which is then transferred to the crude gas from conduit 18. The residual gas then is heated again countercurrently with crude gas in heat exchangers 7 and 3 to 285° K. and leaves the system at a pressure of 4.5 bars.

The turbine power of the expansion turbines 15 and 29 can be utilized, for example, to recompress the residual gas where it is desired to feed it at a higher pressure into a pipeline. In other cases, where the discharge pressure can be lower, and where possibly the supply pressure is also slight, the turbine power can likewise be utilized to compress the crude gas.

This invention is generally useful in case of a high $C_{2+}$ recovery, e.g., above 65%, particularly above 80%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for separating a $C_{2+}$-hydrocarbon fraction from the compressed natural gas by rectification, wherein the compressed natural gas is, prior to rectification, subjected to partial condensation and engine-expansion steps to achieve the desired pressure and temperature conditions in the rectification column and wherein said column is fed by resultant condensate of natural gas, the improvement comprising:

recovering a fluid from the engine expansion step; phase separating said fluid to obtain a liquefied fraction and an unliquefied gaseous fraction, passing said unliquefied gaseous fraction in indirect heat exchange relationship with engine-expanded overhead product from said column, whereby peak cooling and partial condensation of said fraction is achieved, feeding resultant partially condensed unliquefied gaseous fraction to the top of said column, and passing said liquefied fraction from the phase separation step to an intermediate point of said column.

2. A process according to claim 1, further comprising heating the overhead product from the rectification column prior to engine expansion so no condensation takes place during said engine expansion.

3. A process according to claim 2, wherein the overhead product from the rectification column is heated against said unliquefied gaseous fraction.

4. A process according to claim 1, wherein at least one side stream from an intermediate zone of the rectification column is passed in indirect heat exchange with the engine expanded unliquefied fraction of natural gas, thereby utilizing the heat content of the latter to heat the former.

5. A process according to claim 1, wherein a $C_{2+}$ recovery of above 65% is obtained.

6. A process according to claim 1, wherein a $C_{2+}$ recovery of above 80% is obtained.

7. A process according to claim 1 wherein the rectification column comprises a plurality of plates spaced one above another substantially throughout the column.

* * * * *